United States Patent
Katis, Jr.

(10) Patent No.: US 11,071,887 B2
(45) Date of Patent: Jul. 27, 2021

(54) EVALUATION AND COACHING OF ATHLETIC PERFORMANCE

(71) Applicant: Bodbox, Inc., Berkeley, CA (US)

(72) Inventor: Charles William Katis, Jr., Berkeley, CA (US)

(73) Assignee: BODBOX, INC., Berkeley, CA (US)

( * ) Notice: Subject to any disclaimer, the term of this patent is extended or adjusted under 35 U.S.C. 154(b) by 226 days.

(21) Appl. No.: 15/714,195

(22) Filed: Sep. 25, 2017

(65) Prior Publication Data

US 2018/0104541 A1 Apr. 19, 2018

Related U.S. Application Data

(60) Provisional application No. 62/513,123, filed on May 31, 2017, provisional application No. 62/400,928, filed on Sep. 28, 2016.

(51) Int. Cl.
*G09B 19/00* (2006.01)
*A63B 24/00* (2006.01)
(Continued)

(52) U.S. Cl.
CPC ........ *A63B 24/0062* (2013.01); *A61B 5/1123* (2013.01); *A61B 5/1128* (2013.01);
(Continued)

(58) Field of Classification Search
CPC .............. G09B 19/003; G09B 19/0038; A63B 24/0062; A63B 24/0075; A63B 24/065; A63B 24/0068
See application file for complete search history.

(56) References Cited

U.S. PATENT DOCUMENTS

2006/0045312 A1* 3/2006 Bernstein ........... A63B 24/0003
 382/103
2006/0166737 A1 7/2006 Bentley
(Continued)

FOREIGN PATENT DOCUMENTS

CN WO2013084031 A1 6/2013

OTHER PUBLICATIONS

Notification of Transmittal of the International Search Report and the Written Opinion of the International Searching Authority for Int'l Application No. PCT/US2017/053246; dated Jan. 15, 2018.
(Continued)

*Primary Examiner* — Peter R Egloff
(74) *Attorney, Agent, or Firm* — Hamilton, Brook, Smith & Reynolds, P.C.

(57) ABSTRACT

An automated system provides for tracking and evaluation performance of an athlete. An athlete is tracked during performance of a movement, and position data of the performance is applied to an artificial neural network (ANN) trained via a reference data set representing recorded movements. Using the ANN, rank data for the performance is be determined, where the rank data indicates a relationship between the performance of the movement and a subset of the plurality of recorded movements. Based on the rank data, the athlete can be presented with an evaluation of the performance, instructions for subsequent movements and suggestions for improving the athlete's performance.

24 Claims, 7 Drawing Sheets

(51) Int. Cl.
*G06K 9/00* (2006.01)
*A61B 5/11* (2006.01)
*A61B 5/00* (2006.01)
*A63B 71/06* (2006.01)

(52) U.S. Cl.
CPC ........ *A61B 5/7267* (2013.01); *A63B 24/0006* (2013.01); *A63B 71/0622* (2013.01); *G06K 9/00342* (2013.01); *G09B 19/003* (2013.01); *A61B 5/1118* (2013.01); *A61B 2503/10* (2013.01); *A63B 2220/12* (2013.01); *A63B 2220/40* (2013.01); *A63B 2220/836* (2013.01); *A63B 2225/50* (2013.01); *A63B 2230/04* (2013.01)

(56) References Cited

U.S. PATENT DOCUMENTS

| | | | | |
|---|---|---|---|---|
| 2009/0210078 A1* | 8/2009 | Crowley | ................ | G06Q 30/02 700/91 |
| 2010/0173732 A1* | 7/2010 | Vaniche | ............. | A63B 24/0003 473/422 |
| 2012/0277891 A1* | 11/2012 | Aragones | ........... | A61B 5/02438 700/91 |
| 2014/0267611 A1* | 9/2014 | Kennett | ............. | G06K 9/00335 348/46 |
| 2014/0336796 A1* | 11/2014 | Agnew | ................ | A43B 3/0005 700/91 |
| 2014/0342844 A1* | 11/2014 | Mooney | ............. | G06K 9/00342 473/266 |
| 2017/0061817 A1* | 3/2017 | Mettler May | ........ | G09B 19/003 |

OTHER PUBLICATIONS

International Preliminary Report on Patentability for International Application No. PCT/US2017/053246, entitled "Evaluation and Coaching of Athletic Performance", dated Apr. 2, 2019, 9 pages.

* cited by examiner

FIG. 1

REFERENCE DATA SET

| MOVEMENT ID | MOVEMENT DATA | RANK DATA |
|---|---|---|
| MOVEMENT 1 | $M_1$ | [0,2,4] |
| MOVEMENT 2 | $M_2$ | [3,7,1] |
| MOVEMENT 3 | $M_3$ | [0,7,2] |
| ⋮ | ⋮ | ⋮ |
| MOVEMENT N | $M_N$ | [2,2,5] |

COACHING TABLE

| RANK | COACHING INSTRUCTIONS |
|---|---|
| 1 | $C_1$ |
| 2 | $C_3, C_2$ |
| 3 | $C_2, C_4$ |
| ... | ... |
| N | $C_6, C_4$ |

401

MOVEMENT TABLE

| RANK | MOVEMENTS |
|---|---|
| 1 | $W_1, W_4, W_7$ |
| 2 | $W_7, W_3, W_2$ |
| 3 | $W_7, W_9, W_{12}$ |
| ... | ... |
| N | $W_5, W_8, W_{17}$ |

|  | DAY 3 | | | |
|---|---|---|---|---|
|  | Week 1 | Week 2 | Week 3 | Week 4 |
| SMR |  |  |  |  |
| AIS |  |  |  |  |
| NMA |  |  |  |  |
| MS |  |  |  |  |

| | Back Squat | | | | | | | |
|---|---|---|---|---|---|---|---|---|
| Day 1 | x5 | | x5 | | x5 | | x5 | |
| | x5 | | x5 | | x5 | | x5 | |
| | x5 | | x5 | | x5 | | x5 | |
| | x5 | | x5 | | x5 | | x5 | |
| | x5 | | x5 | | x5 | | x5 | |
| | Goblet Lateral Lunge super set | | | | | | | |
| | Sissy Squat 4x50 | | | | | | | |
| | x8 | | x8 | | x8 | | x8 | |
| | x8 | | x8 | | x8 | | x8 | |
| | x8 | | x8 | | x8 | | x8 | |
| | x8 | | x8 | | x8 | | x8 | |

| | Leg Press 15, 10, 10 Drops | | | | | | | |
|---|---|---|---|---|---|---|---|---|
| Day 2 | SL Extensions 15, 10, 10 Drops | | | | | | | |
| | x15 | | x15 | | x15 | | x15 | |
| | x15 | | x15 | | x15 | | x15 | |
| | x15 | | x15 | | x15 | | x15 | |
| | DROP | | DROP | | DROP | | DROP | |
| | Goblet Squat 15, 10, 10 Drops | | | | | | | |
| | Extensions 15, 10, 10 Drops | | | | | | | |
| | x15 | | x15 | | x15 | | x15 | |
| | x15 | | x15 | | x15 | | x15 | |
| | x15 | | x15 | | x15 | | x15 | |
| | FAIL | | FAIL | | FAIL | | FAIL | |

| | 30s ON   15s OFF   3 Rounds |
|---|---|
| Day 3 | Matrix Parachute Run |
| | Atlas Ball Over Shoulder Chains |
| | Hollow Rocking |

EVALUATION AND COACHING OF ATHLETIC PERFORMANCE

RELATED APPLICATIONS

This application claims the benefit of U.S. Provisional Application No. 62/513,123, filed on May 31, 2017; and U.S. Provisional Application No. 62/400,928, filed on Sep. 28, 2016. The entire teachings of the above applications are incorporated herein by reference.

BACKGROUND

Coaching an individual for an athletic pursuit, or other goals relating to fitness, is a subjective practice that typically requires in-person consultation. A coach will observe an athlete's performance and, drawing on experience and expertise, advise the athlete on how to improve his or her performance. The coach might offer suggestions for improving the movements observed by the coach, recommendations for an exercise routine, and advice on diet and nutrition. By harnessing the expertise of a coach, an athlete can make great strides in his or her performance.

SUMMARY

Example embodiments include a method of training an athlete. Position data is generated based on image data of an athlete during performance of a first movement, where the position data indicates position of the athlete over time during the performance of the first movement. The position data may then be applied to an artificial neural network (ANN) trained via a reference data set representing a plurality of recorded movements of a movement category common to the first movement. The reference data set can include position data and a reference rank value for each of the plurality of recorded movements. Using the ANN, a rank value for the performance of the first movement can be determined, where the rank value indicates a relationship between the performance of the first movement and a subset of the plurality of recorded movements. Based on the rank value, instructions for a second movement can be determined, and the athlete can be notified of the instructions. It should be understood that an ANN is an example of a processing technique and that other forms of processing can be employed to perform the operations disclosed herein.

In further embodiments, the second movement may belong in a movement category common to the first movement, and the instructions for the second movement advise the athlete to perform the second movement differently from the performance of the first movement. Further, a performance of the second movement can be captured and processed in a manner comparable to the first movement, providing the athlete with further instructions.

In still further embodiments, the athlete may be notified of a distinction between the performance of the first movement and at least one of the recorded movements. At least one of the recorded movements may have a respective rank value greater than the rank value of the performance of the first movement. The instructions for the second movement may include instructions for traversing the distinction.

In yet further embodiments, the second movement may be of a movement category distinct from the movement category of the first movement. The second movement may include a plurality of subset movements, the instructions specifying 1) a number of repetitions of the subset movements, 2) a time over which to perform the subset movements, and/or 3) a distance over which to perform the subset movements. The instructions may also be based on an input by the athlete identifying a prospective improvement in the performance of the first movement.

Further embodiments may include determining a measure of fatigue of the athlete during the performance of the first movement based on the position data, and instructions for the second movement may be based on the measure of fatigue. Based on the measure of fatigue, an estimation of muscle fiber type for the athlete may be determined. Further, a group of movements may be determined based on the rank value, where the instructions are determined based on the athlete's selection among the group of movements. The reference rank value may be based on a manual assessment of the respective recorded movement. The image data of the athlete may be captured during performance of the first movement. A camera used for capturing the image data of the athlete may be calibrated, where the calibrating includes identifying a color of apparel worn by the athlete.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 1:
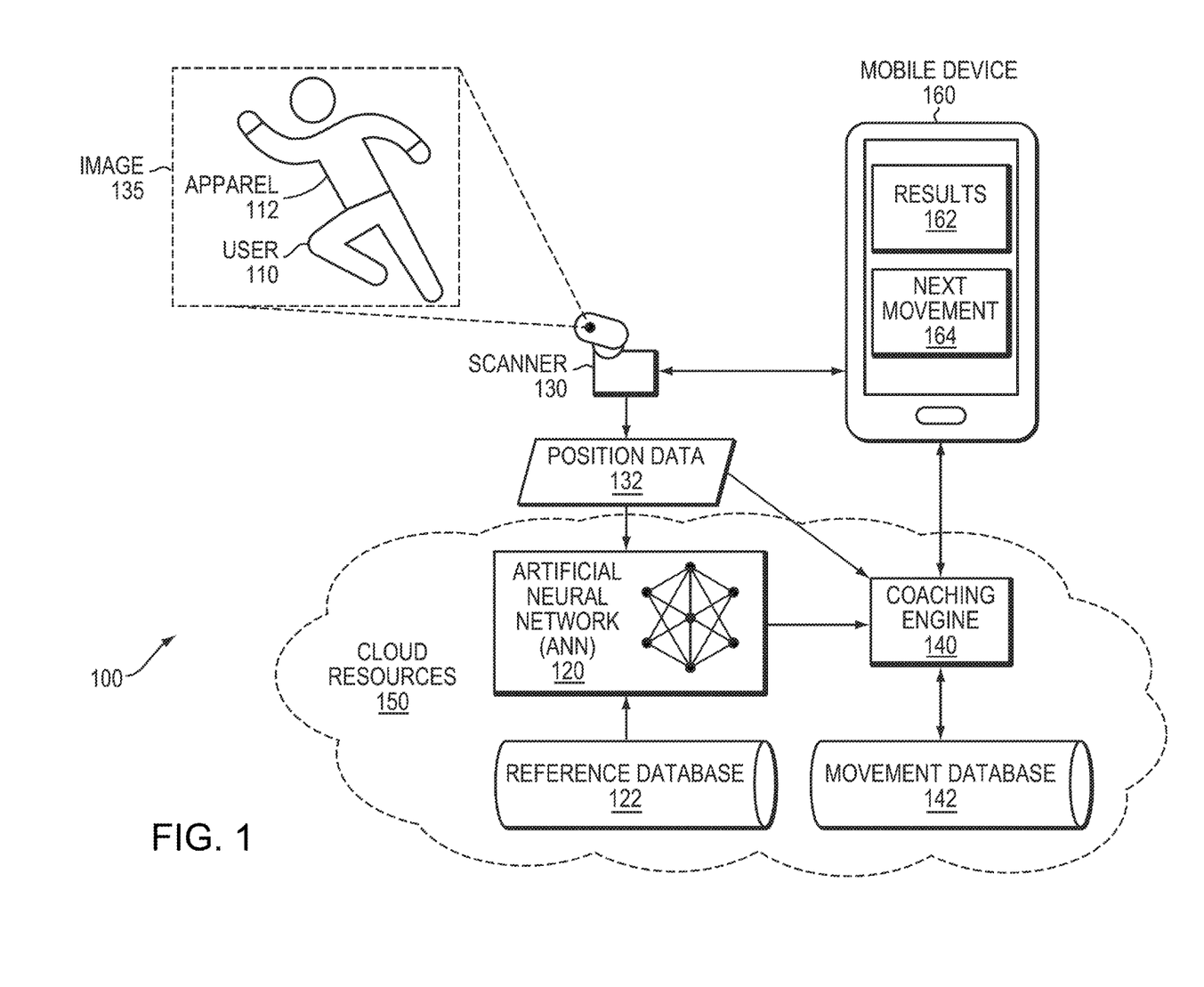
FIG. 1 is a diagram of a coaching system in one embodiment.

FIG. 1 is a diagram of a coaching system 100 in one embodiment. The system 100 may include a scanner 130 and cloud resources 150. A user 110 (also referred to as an athlete) may interface with the system 100 though a mobile device 160 (e.g., a smartphone or tablet, enlarged for clarity), which may be wirelessly communicatively coupled to the scanner 130 and/or the cloud resources 150 via a WiFi, Bluetooth or other communications protocol. The system 100 provides the user 110 with an evaluation of the user's performance of a movement (e.g., a given exercise, workout or fitness test), as well as coaching to improve the user's performance and other aspects of health and fitness.

Prior to a coaching session with the system 100, the user 110 may set up the scanner 130 within a training environment. Specifically, the camera of the scanner 130 may be pointed towards the user 110 so as to capture images of the user 110 during performance of a movement. For example, if the movement to be evaluated is a box jump, the scanner 130 may be configured so that the full range of the user's movement, including the beginning and end of the box jump, are captured within the frame of each image. The scanner 130 may also be calibrated by registering the color or appearance of the user's apparel 112, thereby improving recognition of the user's movements. The user 110 may facilitate this calibration by interacting with the mobile device 160 to complete a calibration process 160. The scanner 130 may include the camera as well as image processing circuitry and a wired or wireless network interface to transmit captured image data. A single-board computer (SBC), such as a Raspberry Pi™ computer, may be implemented in the scanner 130 to provide such processing and interface functions. In alternative embodiments, the mobile device 160 may be implemented in place of, or supplemental to, the scanner 130, where a camera integral to the mobile device 160 captures images of the user's performance.

To initiate a coaching session with the system 100, the user 110 may interact with the mobile device 160. Here, the user 110 may select from a range of different movements to be evaluated, which can be presented as various examinations for physical fitness, muscle fiber type, or a specific movement. Upon selection of a test, the user 110 follows instructions presented on the mobile device 160 to perform the movement. During the performance, the scanner 130 captures images (e.g., image 135) of the user 110 and generates position data 132 representing the user's position in each image. Alternatively, the scanner 130 may simply capture the image data without further processing, instead forwarding the image data to the cloud resources 150 or mobile device 160 to generate the position data 132. A process of image capture and generating the position data 132 is described in further detail below with reference to FIGS. 2A-B.

The cloud resources 150 may include an artificial neural network (ANN) 120, a coaching engine 140, a reference database 122, and a movement database 142. The ANN 120 may be emulated by suitable computing resources, such as a computer server including one or more graphics processing units (GPUs), and may be trained by reference data at the reference database 122. Reference data may include data regarding previously performed movements, as well as evaluation data for those movements. An example reference data set is described in further detail below with reference to FIG. 3. The ANN 120 may include a plurality of distinct sub-ANNs, where each ANN is trained with data of a particular movement category (e.g., box jumps). The position data 132 may be applied to the ANN 120, and, in particular, to the sub-ANN that is trained for the movement category matching the movement performed by the user 110. The ANN 120 processes the position data 132 to determine similarities between the performed movement and the movements represented in the reference data. Based on the determined similarities, the ANN 120 outputs rank data, which identifies such similarities, to the coaching engine 140. For example, the rank data can indicate or include 1) which one or more of the movements represented by the reference data is most similar to the performed movement; 2) a class or subset of the reference movements that is a best match for the performed movement, where each class may correspond to a given characteristic, performance level, or flaw in the movement; or 3) a numerical (e.g., X out of 100) or graded ranking of the performed movement derived from a subjective (e.g., coach-observed) evaluation of the reference movements most similar to the performed movement.

The coaching engine 140 implements the rank data, data about the user (e.g., gender, weight, age, goals, and physical abilities measured in previous coaching sessions), and, optionally, the position data 132, to determine coaching information for the user 110. To do so, the coaching engine 140 may reference the movement database 142. The movement database 142 may store one or more lookup tables cross-referencing rank data and/or position data with coaching information. The coaching information can include coaching instructions (e.g., correction to form of a movement), descriptions of movements (e.g., workout routines), evaluation of the performance (e.g., a "grade" ranking the performance) and/or other suggestions to inform the user 110. Example coaching information is described below with reference to FIG. 4. As a result of referencing the movement database 142, the coaching engine 140 can determine appropriate coaching information for the user 110 and present the information via the mobile device 160. For example, the mobile device 160 may display results 162 of the performance (e.g., time, ranking, grade) and instructions for a next movement 164 (e.g., instructions to correct a deficiency in the performance, a workout routine). The coaching engine 140 may also store the results of the performance, such as rank data and position data 132, to the movement database 142, and may reference those results when evaluating subsequent performances by the user 110.

Figure 2A:
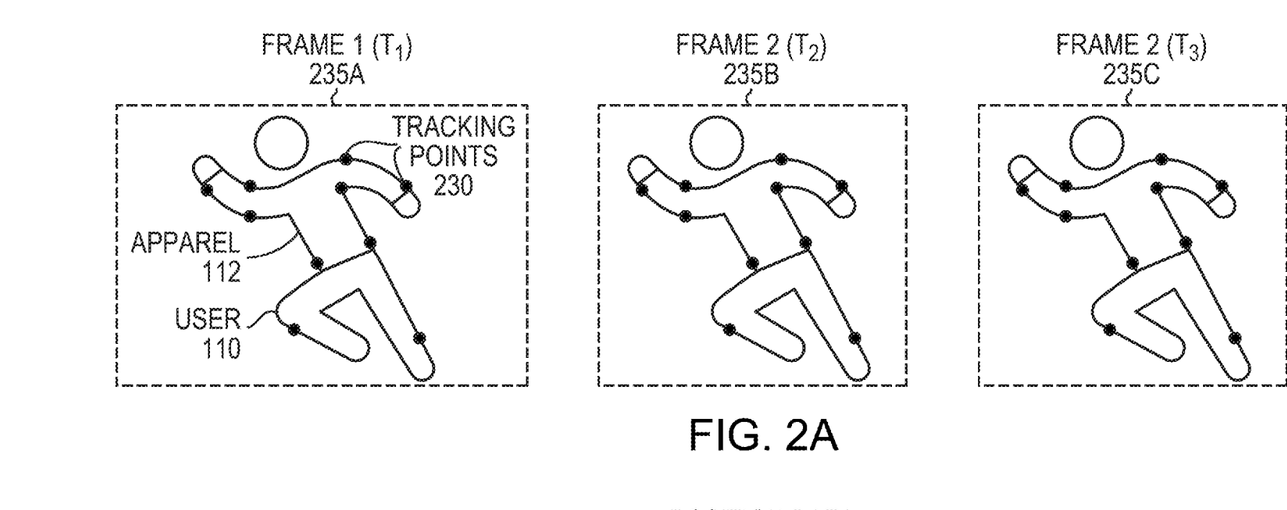
FIG. 2A is a diagram illustrating capture of an athlete's movements.

FIG. 2A is a diagram illustrating detection of the user's position during performance of the movement. Frames 235A-C represent successive images during the performance as captured, for example, by the scanner 130 described above with reference to FIG. 1. The frames 235A-C depict the user 110 moving position relative to the camera's field of view (FOV). In order to track the user's movements, the scanner 130 may identify a plurality of tracking points 230. The tracking points 230 may be designated first during a calibration process as described above, and can be maintained during the user's motion as a result of cross-referencing the user's image between successive images. The scanner 130 may reference the user's apparel 112 to assist in maintaining the tracking points 230, and may identify the apparel 112 by contrast (e.g., color or pattern difference) against other object in the image. For example, the scanner 130 may maintain the tracking points at relative points along a silhouette of the apparel 112 and other portions of the user 110.

Figure 2B:
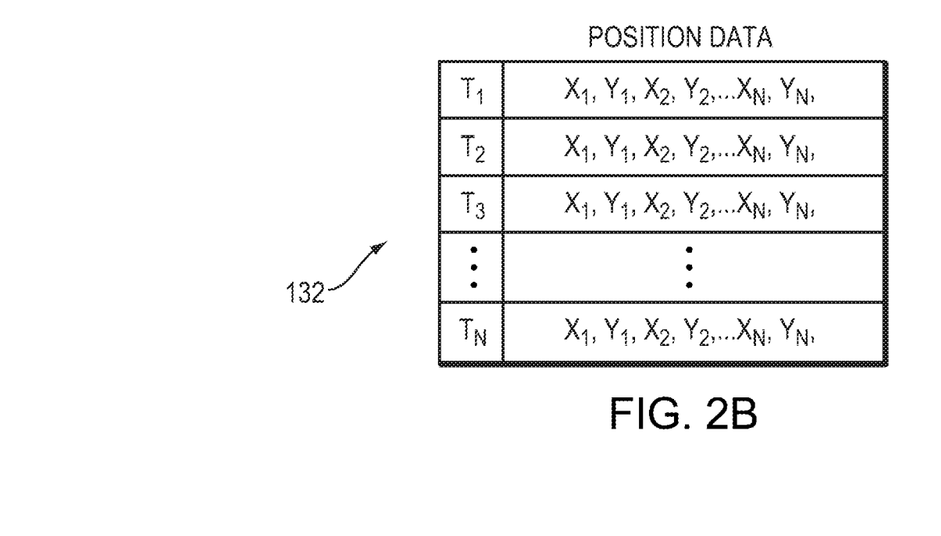
FIG. 2B is a table of position data representing an athlete's movements.

FIG. 2B is a table of the position data 132 representing the user's movements. The first column identifies the time stamp for a given frame (shown as $T_1 \ldots T_N$), and the second column includes coordinates of each of the tracking points 230 in the given frame. For example, the column may include numerical, X-Y coordinates for each of the tracking points 230 (e.g., $X_1, Y_1, X_2, Y_2 \ldots X_N, Y_N$) as they are delineated in the 2D plane of the frame. The X-Y coordinates may be captured as the pixel coordinates of the given frame, and may be entered into the ANN 120 or may first be translated to physical coordinates (e.g., via the use of an object of known size to provide a scale, or via an estimate based on the recorded velocity of the movement). Alternatively, if the scanner 130 (alone or in combination with another device, such as the mobile device 160) captures stereoscopic or other 3D image data of the user 110, then the position data 132 may include 3D coordinates of the tracking points 230. 3D image data, in particular, can aid in determining the physical coordinates of the tracking points 230 through the movement.

Figure 3:
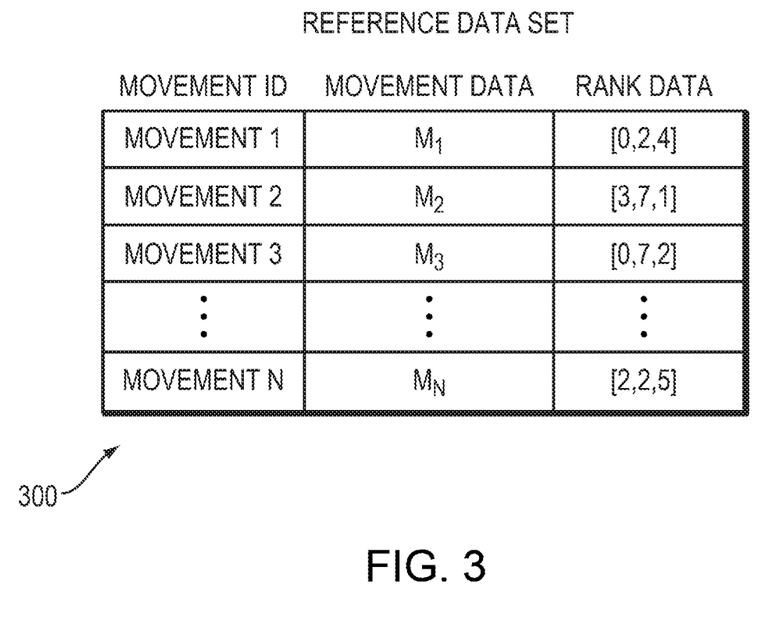
FIG. 3 is a table of a reference data set including movement data.

FIG. 3 is a table of a reference data set 300. The reference data set 300 may be stored in the reference database 122 of FIG. 1, and may be employed to train the ANN 120. The reference data set 300 may be specific to a particular movement category, wherein all of the entries represent movements of a common type (e.g., a box jump). For example, each entry may represent a previously recorded demonstration of the movement, which may have been captured by a process comparable to that described above with reference to the system 100. In order to provide coaching and evaluation for a range of different movements, the reference database 122 may include a plurality of different reference data sets, each data set pertaining to a different movement category. Each reference data set can be implemented to train a respective ANN.

The reference data set 300 includes a first column including a "movement identifier" (ID) for each of the represented movements. A second column stores movement data, which includes information about the movement. The movement data can include, for example, data comparable to the position data 132 shown in FIG. 2B, including a succession of tracking point coordinates and respective timestamps. In order to optimize the training of the ANN 120, the movement data may be recorded by means comparable to that by which the position data 132 is recorded (e.g., via the scanner 130 or a comparable device, and the recorded athlete following instructions comparable to those presented to the user 110 prior to the performance). As a result, the ANN 120 may be sufficiently adapted to identify parallels between the position data 132 and the reference data set 300.

A third column of the reference data set 300 stores rank data. The rank data for each movement may include numerals or other code identifying objective and/or subjective information about the movement. For example, a first numeral may identify a "grade," or subjective evaluation, or the movement as determined by a human coach observing the movement. This evaluation may also correspond to a ranking (e.g., a percentile value) of the movement relative to other movements. A second numeral may identify one or more flaws in the movement, such as a deficiency in technique, as determined by the coach. A third numeral may identify objective information about the movement, such as the identity of the athlete performing the movement, or the total time in which the movement was completed. A fourth numeral may identify information about the athlete performing the movement, such as the athlete's muscle fiber type.

The ANN 120, being trained with the reference data set 300, processes the user's position data 132 to identify parallels between the position data 132 and the reference data set 300. As a result, the ANN 120 determines appropriate rank data for the position data 132. This data, referred to as user rank data, is output by the ANN 120 to the coaching engine 140. The coaching engine 140, in turn, applies the user rank data to one or more lookup tables to determine appropriate evaluation and coaching information corresponding to the user's performance. Example lookup tables are described in further detail with reference to FIG. 4 below.

Figure 4:
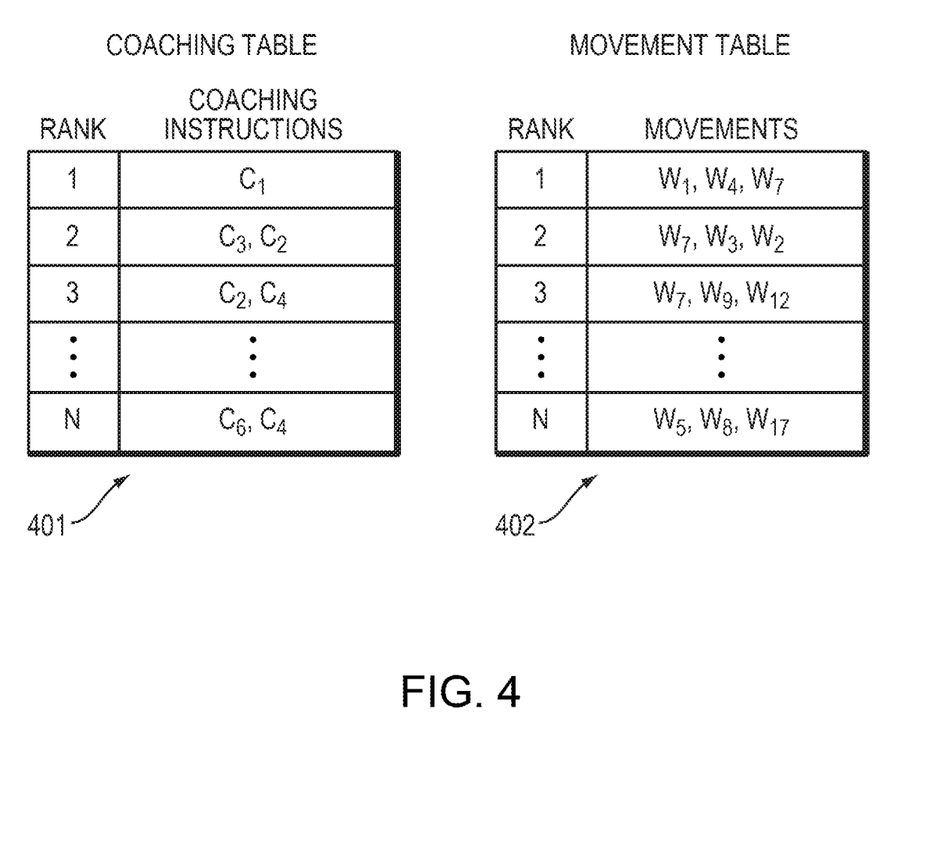
FIG. 4 illustrates tables of instructions to a user.

FIG. 4 illustrates lookup tables 401, 402 for cross-referencing rank data and coaching information. With reference to FIGS. 1 and 3, the coaching engine 140 may apply the user rank data to the tables 401, 402. The coaching table 401 correlates a rank value with coaching instructions ($C_1$-$C_N$), which represent instructions that may be provided to a user 110 to improve the users performance. For example, instruction $C_1$ may correspond to suggestions for modifying the user's form when performing the movement, and instruction $C_2$ may correspond to a suggestion for a pre-performance action (e.g., a stretch or mobility work) to improve the user's range of motion. To optimize data storage, the table 401 may store pointers to instructions rather than the instructions themselves, where $C_1$-$C_N$ point to the instructions located in another table (not shown) stored in the movement database 142 or another database.

The movement table 402 correlates a rank value (which may be distinct from the rank values applied to the coaching table 401) with movements ($W_1$-$W_N$), which represent a range of suggestions that may be presented to the user 110. For example, $W_1$ may correspond to a variation of the movement performed by the user 110, $W_2$ may correspond to a structured interval training routing, $W_3$ may correspond to a structured strength training routine, $W_4$ may correspond to a mobility routine, $W_5$ may correspond to an endurance training routine (e.g., swimming, distance running), and $W_6$ may correspond to a diet recommendation. Similarly to the table 401, the table 402 may store pointers to the above movements as located in another table (not shown).

Upon applying the user rank values to the tables 401, 402, the coaching engine 140 may compile the corresponding coaching instructions and movements and present them to the user 110 via the mobile device 160, and may be included in the results 162 and next movement 164. If the coaching engine 140 presents a suggested movement that can be tracked by the system 100, and the user 110 selects that movement, then the system 100 may carry out a subsequent process of tracking and evaluating the user's performance of the suggested movement. The coaching engine 140 can also present the user rank data directly (e.g., a rank value that indicates a grade or percentile of the performance), can present objective measurements of the performance based on the position data 132 (e.g., time completed, velocity, acceleration), or can apply the user rank data to other lookup tables or data sources to present other information to the user 110. For example, the user rank data and/or position data 132 may be compared against data regarding previous performances by the user 110 to determine whether how the user's performance has changed or improved. Similarly, the user rank data and/or position data 132 may be compared against data regarding performances by other athletes, informing the user 110 how his/her performance compares to those performances.

In a further embodiment, the coaching engine 140 may estimate the muscle fiber composition of the user 110 based on the position data 132 and/or user rank data. The user rank data may include such an estimate directly (e.g., as a result of the ANN 120 being trained with known muscle fiber types included in the reference data set 300), or may be calculated based on the position data 132.

Figure 5:
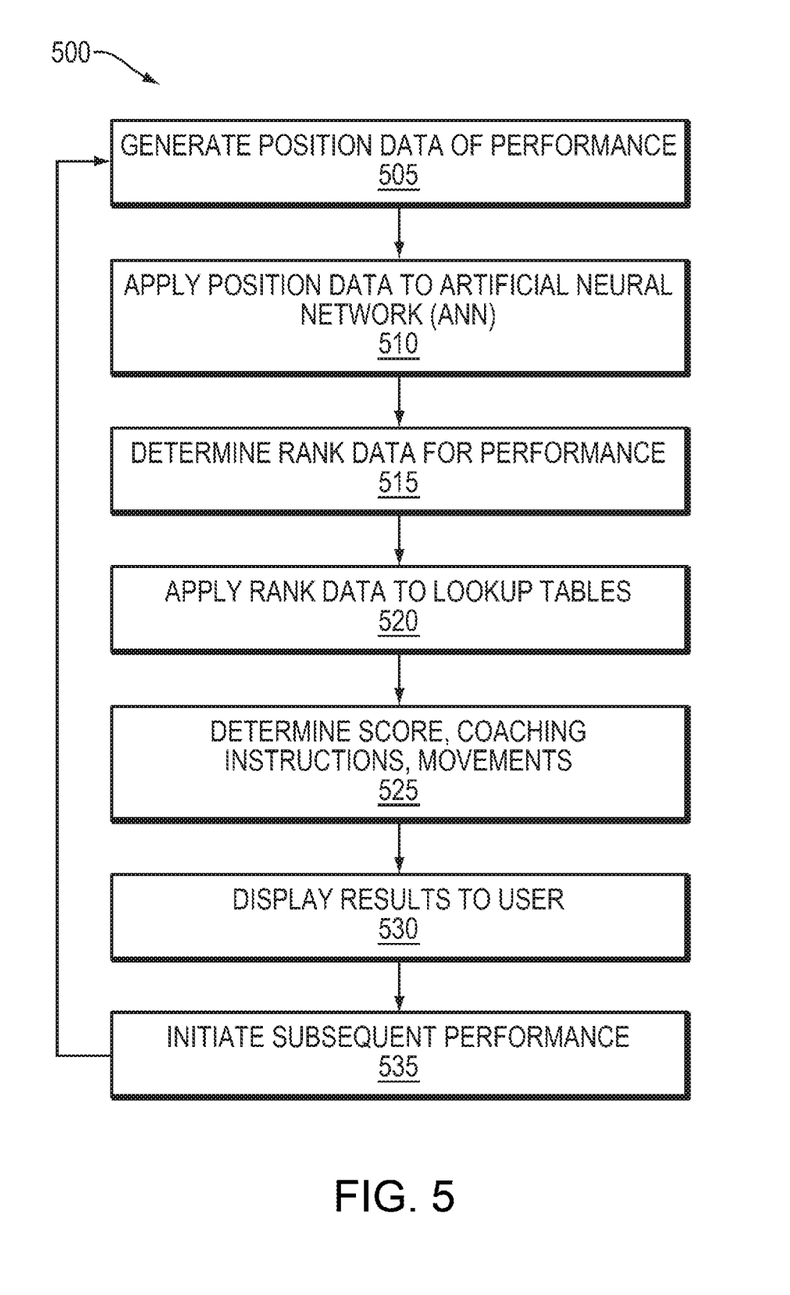
FIG. 5 is a flow diagram of a method of training an athlete in one embodiment.

FIG. 5 is a flow diagram of an example process 500 of training an athlete in one embodiment. The process 500 may be implemented by the system 100 of FIG. 1, and may incorporate one or more of the features described above with reference to FIGS. 1-4. Upon initiating a coaching session, the scanner 130 captures images of the user's performance in completing a movement, and generates corresponding position data 132 (505). The position data 132 is uploaded to the cloud resources 150, where it is applied to the ANN 120 trained on a reference data set 300 of a common movement category (510). Through the ANN 120, the user rank data for the performance is determined (515). The coaching engine 140 then applies the user rank data to lookup tables 401, 402 (520), and determines a performance score, coaching instructions and suggestions for movements (e.g., structured workout routines) (525). The results are then presented to the user 110 at the mobile device 160 (e.g., results 162 and next movement 164) (530). If the user 110 selects the next movement 164 for evaluation, then a subsequent performance is initiated (535), and the process 500 is repeated to evaluate the subsequent performance.

Further embodiments may be configured to provide coaching in physical therapy applications. In such an application, as well as in other training applications, the process 500 may be initiated after a user 110 selects a movement (e.g., a rehabilitation movement) to perform from a menu of movements presented at a user interface (e.g., mobile device 160). The operations of analyzing the recorded movement (510-525) may be configured to identify and coach specific flaws in the movement related to given injuries from which the user 110 may be recovering. Accordingly, the results displayed to the user 110 (530) may include particular guidance for improving the movement, such as range of motion, velocity, subjective quality of movement based on comparable reference movements, and coaching suggestions for movements and exercises to improve the user's performance.

Figure 6:
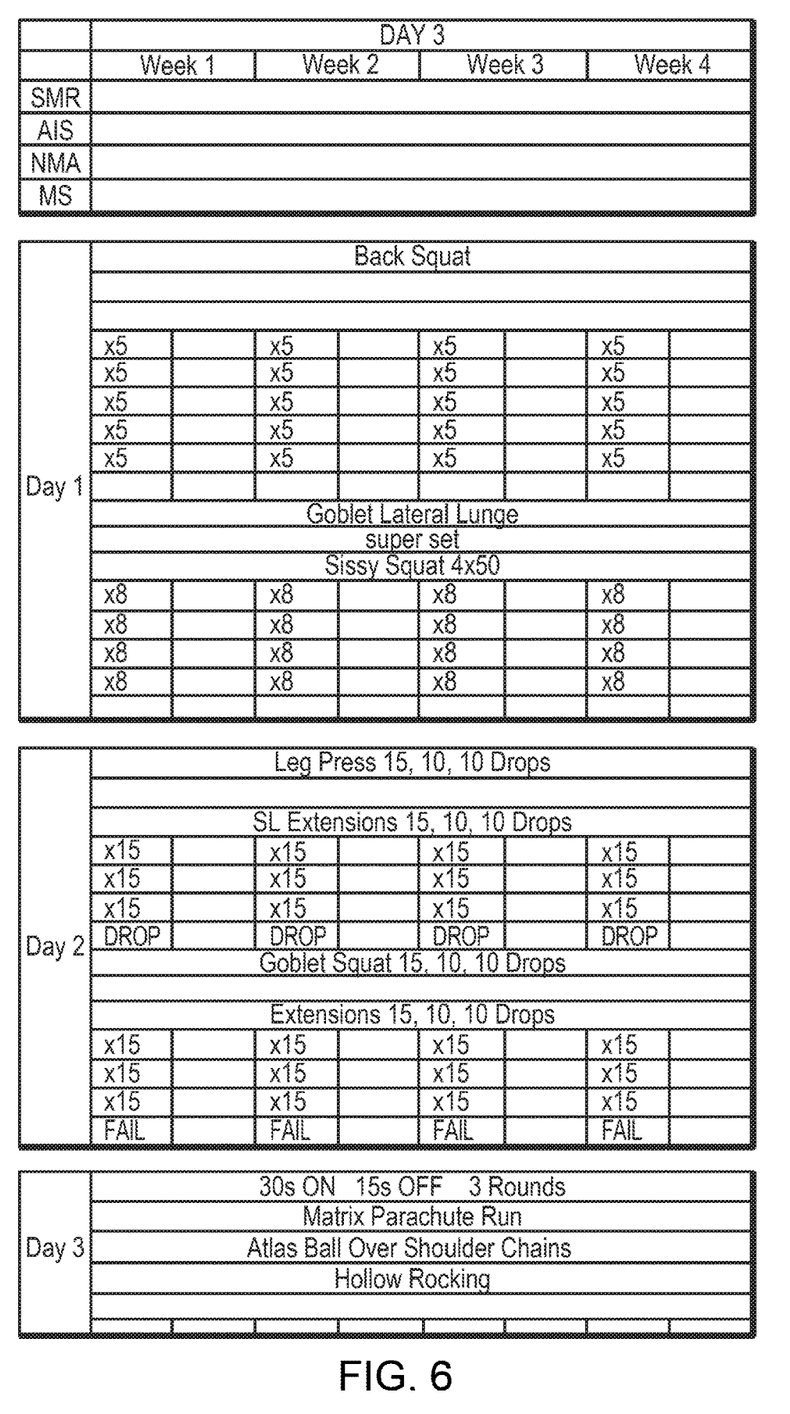
FIG. 6 is a screenshot of a display including workout information.

FIG. 6 is a screenshot of a display including workout information. The workout information may include a structured workout routine, including a listing of movements to be performed, as well as a calendar organizing the timing of the routine. The workout information may be configured by the coaching engine 140, and may be based on suggested movements retrieved from the lookup table 402. The display may also include spaces where the user 110 can manually enter results of the workout (e.g., weight lifted, time completed).

Figure 7:
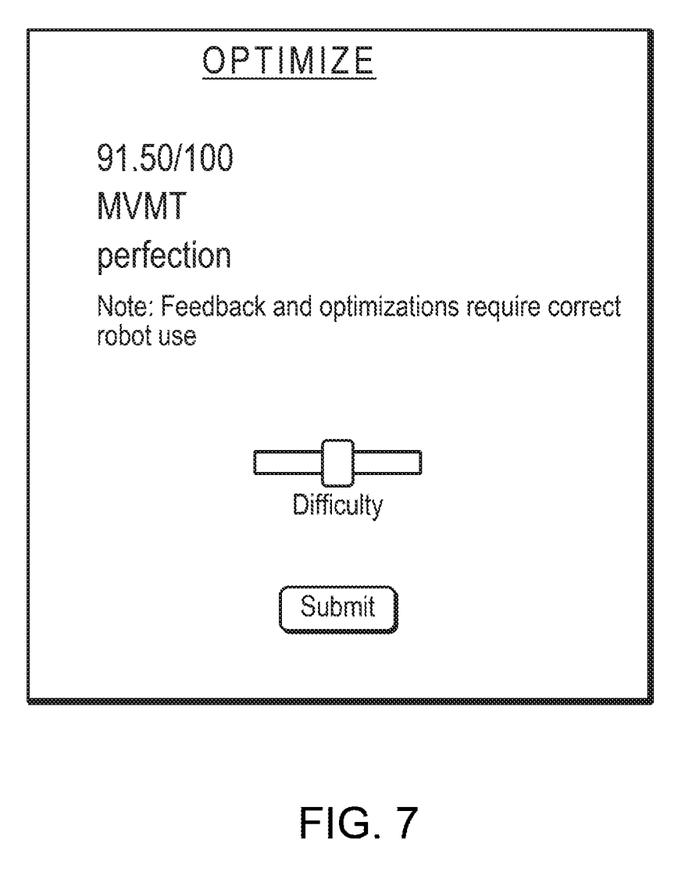
FIG. 7 is a screenshot of a display including results of analyzing an athlete's movement.

FIG. 7 is a screenshot of a display including results of evaluating an athlete's performance. The display includes a score ("91.50/100") for the performance of a movement, which may be derived from the user rank data, the position data 132, and/or a lookup table (e.g., tables 401, 402). The display also includes a difficulty slider, enabling the user 110 to select a relative difficulty for the next movement to perform. In response to this selection, the coaching engine 140 may modify established movements from the movement database 142 to create a movement having higher or lower difficulty.

Example embodiments may include a computer program product, including a non-transitory computer-readable medium (e.g., a removable storage medium such as one or more DVD-ROM's, CD-ROM's, diskettes, tapes, etc.) that provides at least a portion of the software instructions for the invention system. The computer program product can be installed by any suitable software installation procedure, as is well known in the art. In another embodiment, at least a portion of the software instructions may also be downloaded over a cable communication and/or wireless connection.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of training an athlete, comprising:

generating position data based on image data of an athlete during a first performance of a movement, the position data including pixel coordinates of a plurality of tracking points associated with the athlete for multiple frames of the image data, the position data indicating position of the athlete over time during the first performance of the movement;

applying the position data to an artificial neural network (ANN) trained via a reference data set representing a plurality of recorded performances of the movement, the reference data set including position data and a reference rank value for each of the plurality of recorded performances;

identifying, via the ANN, a correlation between the position data and at least one of the recorded performances of the movement;

determining, via the ANN, a rank value for the performance of the first movement based on the correlation, the rank value indicating a relationship between the first performance of the movement and a subset of the plurality of recorded performances;

applying the rank value to a table to identify coaching instructions corresponding to the rank value, the table cross-referencing a plurality of rank values and coaching instructions corresponding to each of the plurality of rank values;

determining instructions for a second performance of the movement by selecting from the coaching instructions corresponding to the rank value, the second performance corresponding to the first performance with the exception of a correction to form of the first performance, the instructions for the second performance including instructions to perform the second performance in a manner distinct from the first performance; and notifying the athlete of the instructions for the second performance of the movement.

2. The method of claim 1, further comprising:

capturing image data of an athlete during the second performance of the movement;

determining, via the ANN, a rank value for the second performance of the movement, the rank value indicating a relationship between the second performance of the movement and a subset of the plurality of recorded performances;

comparing the rank values of the first and second performances; and notifying the athlete based on the comparison.

3. The method of claim 1, further comprising notifying the user of a distinction between the first performance and at least one of the recorded performances.

4. The method of claim 3, wherein the at least one of the recorded performances has a respective rank value greater than the rank value of the first performance.

5. The method of claim 3, wherein the instructions for the second performance include instructions for traversing the distinction.

6. The method of claim 1, further comprising determining instructions for a further movement based on the rank value, the further movement being of a movement category distinct from the movement category of the movement.

7. The method of claim 1, wherein the second performance includes a plurality of subset movements, the instructions specifying at least one of 1) a number of repetitions of the subset movements, 2) a time over which to perform the subset movements, and 3) a distance over which to perform the subset movements.

8. The method of claim 1, wherein determining the instructions for the second performance is further based on an input by the athlete identifying a prospective improvement in the first performance.

9. The method of claim 1, further comprising determining a measure of fatigue of the athlete during the first performance based on the position data.

10. The method of claim 9, wherein determining instructions for the second performance is based on the measure of fatigue.

11. The method of claim 9, further comprising determining an estimation of muscle fiber type for the athlete based on the measure of fatigue.

12. The method of claim 1, further comprising determining a group of movements based on the rank value, and further comprising determining a further movement based on a selection, by the athlete, of the further movement from among the group of movements.

13. The method of claim 1, wherein the reference rank value is based on a manual assessment of the respective recorded performance.

14. The method of claim 1, further comprising capturing the image data of the athlete during the first performance.

15. The method of claim 14, further comprising calibrating a camera used for capturing the image data of the athlete, the calibrating including identifying a color of apparel worn by the athlete.

16. A computer-implemented method of training an athlete, comprising:
    generating position data based on image data of an athlete during performance of a first movement, the position data including pixel coordinates of a plurality of tracking points associated with the athlete for multiple frames of the image data, the position data indicating position of the athlete over time during the first performance of the first movement;
    applying the position data to an artificial neural network (ANN) trained via a reference data set representing a plurality of recorded performances of the movement, the reference data set including position data and a reference rank value for each of the plurality of recorded performances;
    identifying, via the ANN, a correlation between the position data and at least one of the recorded performances of the movement;
    determining, via the ANN, a rank value for the performance of the first movement based on the correlation, the rank value indicating a relationship between the performance of the first movement and a subset of the plurality of recorded performances;
    applying the rank value to a table to identify coaching instructions corresponding to the rank value, the table cross-referencing a plurality of rank values and coaching instructions corresponding to each of the plurality of rank values;
    determining a group of distinct movements by selecting from the coaching instructions corresponding to the rank value;
    determining instructions for a second movement based on a selection, by the athlete, among the group of distinct movements; and
    notifying the athlete of the instructions for the second movement.

17. The method of claim 16, wherein the second movement is of a movement category distinct from the movement category of the first movement.

18. The method of claim 16, wherein the second movement includes a plurality of subset movements, the instructions specifying at least one of 1) a number of repetitions of the subset movements, 2) a time over which to perform the subset movements, and 3) a distance over which to perform the subset movements.

19. The method of claim 16, wherein the reference rank value is based on a manual assessment of the respective recorded performance.

20. The method of claim 16, further comprising determining a measure of fatigue of the athlete during the performance of the first movement based on the position data.

21. A system for training an athlete, comprising:
    an artificial neural network (ANN) trained via a reference data set representing a plurality of recorded performances of the movement, the reference data set including position data and a reference rank value for each of the plurality of recorded performances;
    a server configured to communicate with a scanner and a computing device across a network, the server configured to:
        generate position data based on image data captured by the scanner of an athlete during a first performance of a movement, the position data including pixel coordinates of a plurality of tracking points associated with the athlete for multiple frames of the image data, the position data indicating position of the athlete over time during the first performance of the movement;
        apply the position data to the ANN;
        identify, via the ANN, a correlation between the position data and at least one of the recorded performances of the movement
        determine, via the ANN, a rank value for the performance of the first movement based on the correlation, the rank value indicating a relationship between the first performance of the movement and a subset of the plurality of recorded performances;
        applying the rank value to a table to identify coaching instructions corresponding to the rank value, the table cross-referencing a plurality of rank values and coaching instructions corresponding to each of the plurality of rank values;
        determine instructions for a second performance of the movement selecting from the coaching instructions corresponding to the rank value, the second performance corresponding to the first performance with the exception of a correction to form of the first performance, the instructions for the second performance including instructions to perform the second performance in a manner distinct from the first performance; and
        transmit the instructions for the second performance of the movement to the computing device.

22. The system of claim 21, wherein the server is further configured to transmit to the computing device a notification of a distinction between the performance of the first movement and at least one of the recorded performances.

23. The system of claim 22, wherein the at least one of the recorded performances has a respective rank value greater than the rank value of the first performance of the movement.

24. The system of claim 22, wherein the instructions for the second performance include instructions for traversing the distinction.

* * * * *